United States Patent [19]

Parker

[11] Patent Number: 4,770,299

[45] Date of Patent: Sep. 13, 1988

[54] ROLL FORM MEDICAL BANDAGING PRODUCT

[75] Inventor: A. Bruce Parker, Charlotte, N.C.

[73] Assignee: Parker Medical Associates, Charlotte, N.C.

[21] Appl. No.: 815

[22] Filed: Jan. 6, 1987

[51] Int. Cl.$^4$ .................... B65D 85/66; B65D 85/671
[52] U.S. Cl. ..................................... 206/409; 128/90; 128/156; 128/169; 206/389; 206/440; 428/36; 428/74
[58] Field of Search ...................... 128/89 R, 90, 91 R, 128/156, 169; 206/411, 412, 413, 447, 484, 440, 484.2, 389, 409; 427/2; 428/36, 74

[56] References Cited

U.S. PATENT DOCUMENTS

| | | | |
|---|---|---|---|
| 2,940,884 | 6/1960 | White | 206/447 |
| 3,557,156 | 1/1971 | Enneper et al. | 604/358 |
| 3,900,024 | 8/1975 | Lauber et al. | 128/91 |
| 3,923,049 | 12/1975 | Lauber et al. | 128/91 |
| 4,235,228 | 11/1980 | Gaylord et al. | 128/91 |
| 4,279,344 | 7/1981 | Holloway, Jr. | 206/484 |
| 4,411,262 | 10/1983 | von Bonin et al. | 128/90 |
| 4,427,002 | 1/1984 | Baron et al. | 128/83 |
| 4,433,680 | 2/1984 | Yoon | 128/90 |
| 4,442,833 | 4/1984 | Dahlen et al. | 128/90 |
| 4,502,479 | 3/1985 | Garwood et al. | 128/90 |
| 4,570,622 | 2/1986 | von Bonin et al. | 128/90 |
| 4,572,171 | 2/1986 | Wegner et al. | 128/90 |
| 4,676,861 | 6/1987 | Bishop | 206/411 |

FOREIGN PATENT DOCUMENTS 2004752 11/1969 France ........................... 206/412

0630022 10/1961 Canada ............................ 206/440

OTHER PUBLICATIONS

"Plaster Splints Aren't What They're Cracked Up to Be", Eudurasplint brochure, Carapace Inc. (1987).
Brochure on Universal Plaster Splinting (1986)-Zimmer, Inc.
C-Splint Immobilizer (1982) (Cutter Laboratories, Inc.).
Scotchcast 2 Splinting System (Undated) (Orthopedic Products Division, Minnesota Mining & Manufacturing Company).

Primary Examiner—Richard J. Apley
Assistant Examiner—Paul Prebilic
Attorney, Agent, or Firm—W. Thad Adams, III

[57] ABSTRACT

A medical bandaging product (10) is rolled into a coil and positioned in a dispenser (11). Bandaging product (10) includes an outer elongate sleeve (13) formed of a moisture-impervious material and heat sealed along opposite, parallel extending sides to form an elongate tube. A medical material (14) is positioned within sleeve (13) and includes a substrate (16) formed of a suitable number of overlaid layers of a woven or knitted fabric such as fiberglass. Substrate (16) is contained within a tubular wrapping (18) formed of a soft, flexible nonwoven fiber such as polypropylene. Substrate (16) is impregnated or coated with a reactive system which remains stable when maintained in substantially moisture-free conditions but which hardens upon exposure to sufficient moisture to form a rigid, self-supporting structure.

11 Claims, 4 Drawing Sheets

4,770,299

ROLL FORM MEDICAL BANDAGING PRODUCT

TECHNICAL FIELD AND BACKGROUND OF THE INVENTION

The present invention relates generally to the field of orthopedic medicine and more specifically to the design of an improved medical bandage formed of a moisture-curable plastic material and a method for constructing such an improved medical bandage.

Medical bandages for use in the treatment of injuries, such as broken bones requiring immobilization of a body member, are generally formed from a strip of fabric or scrim material impregnated with a substance which hardens into a rigid structure after the strip has been wrapped around the body member. The hardening substance traditionally used in carrying out this procedure is plaster-of-paris.

Conventional practice has been to fabricate a cast or splint upon an injured limb by initially applying to the limb a protective covering of a cotton fabric or the like and then overwrapping the covering and limb with a woven cloth impregnated with plaster-of-paris which has been wetted by dipping in water immediately prior to application. This practice is still in widespread use but possesses several significant disadvantages. For example, the above-described application procedure is messy and time consuming. Several components are required and considerable skill is necessary.

In order to alleviate the above-recited disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris cast materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult. Even if wetting due to these causes can be avoided, perspiration over an extended period of time can break down the plaster-of-paris and create a significant problem with odor and itching.

A significant advance in the art of casting and splinting is disclosed in U.S. Pat. Nos. 4,411,262 and 4,502,479. The casting materials disclosed in these patents comprise a flexible fabric impregnated with a moisture-curing resin enclosed in a moisture-free, moisture-impervious package. Compared to plaster-of-paris, these products are extremely lightweight, have a very high strength to weight ratio and can be made relatively porous, permitting a flow of air through the casting material. Prior art moisture-curing systems include a package within which is contained a plurality of layers of fabric, such as fiberglass, impregnated with a moisture-curing resin. No provision is made for reclosing the package, so that the entire material must be very quickly used after removal from the package since such moisture-curing resins will cure in a relatively short period of time due merely to contact with atmospheric moisture.

From the above discussion, it can be seen that both the conventional plaster-of-paris casting method and the more recent moisture-curable resin casting method possess both advantages and disadvantages. On the one hand, plaster-of-paris casts are bulky, heavy and difficult to apply whereas moisture-curable resin casts are lightweight, durable and relatively easy to apply. Plaster-of-paris can be very easily stored and used as needed since it has a relatively long shelf life so long as it is not completely wetted. On the other hand, the moisture-curable resins are very sensitive to the presence of even minute amounts of moisture which requires that either the materials be packaged in a wide variety of different shapes and sizes or unused portions be discarded, generating a substantial amount of waste and increasing the effective cost of the product. This invention combines the advantages of both plaster-of-paris and moisture-curable resin systems while avoiding their respective disadvantages. This is accomplished by providing a unitary splinting system with improved strength and convenience. A unitary system is provided with the use of moisture-curing resin casting materials, together with a moisture-impervious package with means for resealing the package against entry of moisture after a desired length of bandaging product has been removed for use. In this manner, hardening of the bandaging product remaining in the moisture-impervious package is prevented thereby increasing the cost effectiveness of the system substantially.

SUMMARY OF THE INVENTION

It is therefore an object of the invention to provide a medical bandaging product in roll form with a moisture-curable resin which hardens the material upon exposure to moisture to form a rigid, self-supporting structure.

It is another object of the invention to provide a medical bandaging product which can be dispensed in any desired length while preventing hardening of the remaining material until use is desired.

It is another object of the invention to provide a unitary medical bandaging product which includes a wrapping to provide a cushion against the skin of a patient.

It is another object of the invention to provide a method of constructing a medical bandaging product having the characteristics and objects described above.

These and other objects and advantages of the present invention are achieved in the preferred embodiment disclosed below by providing a medical bandaging product in roll form for being dispensed in predetermined length suitable for a given medical use. The product comprises an elongate sleeve formed of moisture-impervious material and sealable to prevent entry of moisture. An elongate medical material is positioned within the sleeve and sealed therein against entry of moisture until use. The medical material comprises a substrate impregnated or coated with a reactive system which remains stable when maintained in substantially moisture-free conditions but hardens upon exposure to sufficient moisture to form a rigid, self-supporting structure. A soft, flexible protective wrapping encloses the substrate along its length to provide a cushioning barrier between the substrate and the skin of a patient when the material is in use. Means, such as a moisture-impervious tape, is provided for resealing the sleeve against entry of moisture after a predetermined length of the bandaging product has been dispensed for use to prevent hardening of the substrate remaining in the sleeve until use is desired.

The substrate preferably comprises a plurality of knitted or woven fabric layers of a material such as fiberglass.

The protective wrapping which encloses the substrate preferably comprises a non-woven cushion formed of polypropylene or some other hydrophobic fiber in the form of a tube within which the substrate is placed.

Preferably, the medical bandaging product is rolled into a coil and positioned in a dispenser having a slot through which the product is dispensed as needed.

In accordance with the method according to the present invention, an elongate sleeve, an elongate medical material comprised of a substrate and soft, flexible wrapping is provided. The substrate is impregnated with a reactive system which remains stable when maintained in substantially moisture-free conditions and hardens upon exposure to sufficient moisture to form a rigid, self-supporting structure. The substrate is enclosed within the soft, flexible wrapping and then positioned in said elongate sleeve. The sleeve is sealed to prevent entry of moisture.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DESCRIPTION OF THE PREFERRED EMBODIMENT

Figure 1:
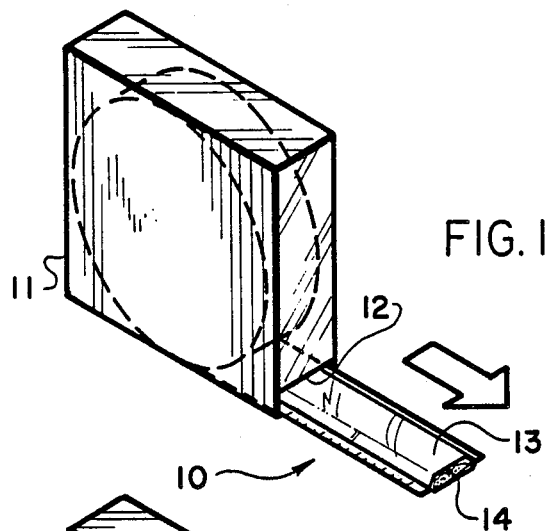
FIG. 1 is a perspective, schematic view showing the medical bandaging product being dispensed from a dispenser.

Referring now specifically to the drawings, a medical bandaging product according to the present invention is shown generally in FIG. 1 at 10. Bandaging product 10 may be sold in any convenient length, such as 24 feet, and is rolled into a coil and positioned in a suitable dispenser 11. Dispenser 11 is provided with a slot 12 at one lower corner through which bandaging product 10 extends.

Bandaging product 10 is comprised generally of an outer elongate sleeve 13 which is formed of a moisture-impervious material. Sleeve 13 is heat sealed along opposite, parallel extending sides to form an elongate tube. An elongate medical material 14, described in detail below, is positioned within sleeve 13 and is maintained in substantially moisture-free conditions until dispensed.

Figure 2:
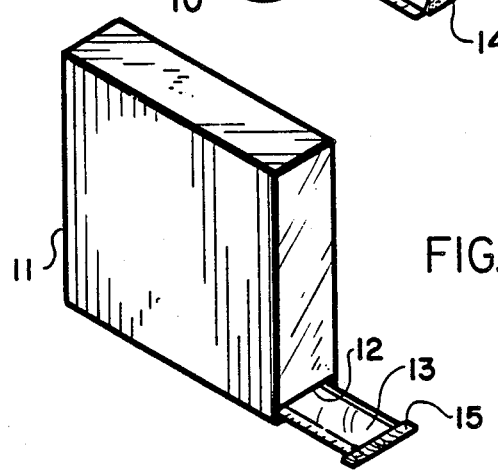
FIG. 2 is a view similar to FIG. 1, showing the unused portion of the medical bandaging product being resealed to prevent entry of moisture.

As is shown in FIG. 2, the end of sleeve 13 is sealed with sealing means, such as a moisture-impervious tape 15.

Other types of sealing mechanisms are possible such as, for example, a soft, conformable gasketing device with spring loaded compression, leverage clamping or screw action of sufficient strength to prevent entry of moisture into sleeve 13. One particularly suitable device (not shown) is a pair of spring loaded rollers which, as compression takes place rolls slightly backwards, pushing medical material 14 back slightly into sleeve 13 to permit a better seal.

Another possible sealing means (not shown) is a device which pushes the medical material 14 back into the sleeve 13 a sufficient distance (approximately one inch), so that the open end of sleeve 13 may be heat sealed once again.

Figure 3:
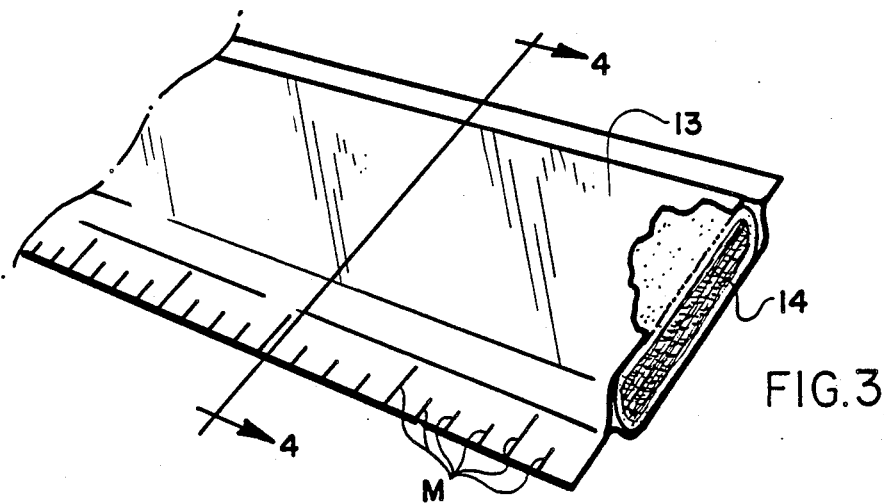
FIG. 3 is a perspective view with parts broken away of a cut length of medical material.

Since the appropriate length of medical material 14 is best determined by measurement, measurement marks "M" are printed on one edge of the sleeve 13, as is best shown in FIG. 3. Once the appropriate length of medical material 14 has been dispensed and cut from the roll, it is removed from sleeve 13 and sleeve 13 is discarded.

Figure 4:
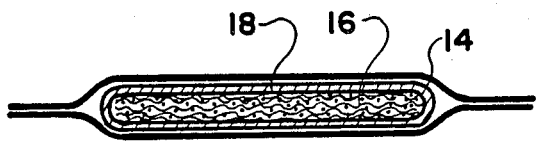
FIG. 4 is a vertical cross-section taken substantially along lines 4—4 of FIG. 3.
Figure 5:
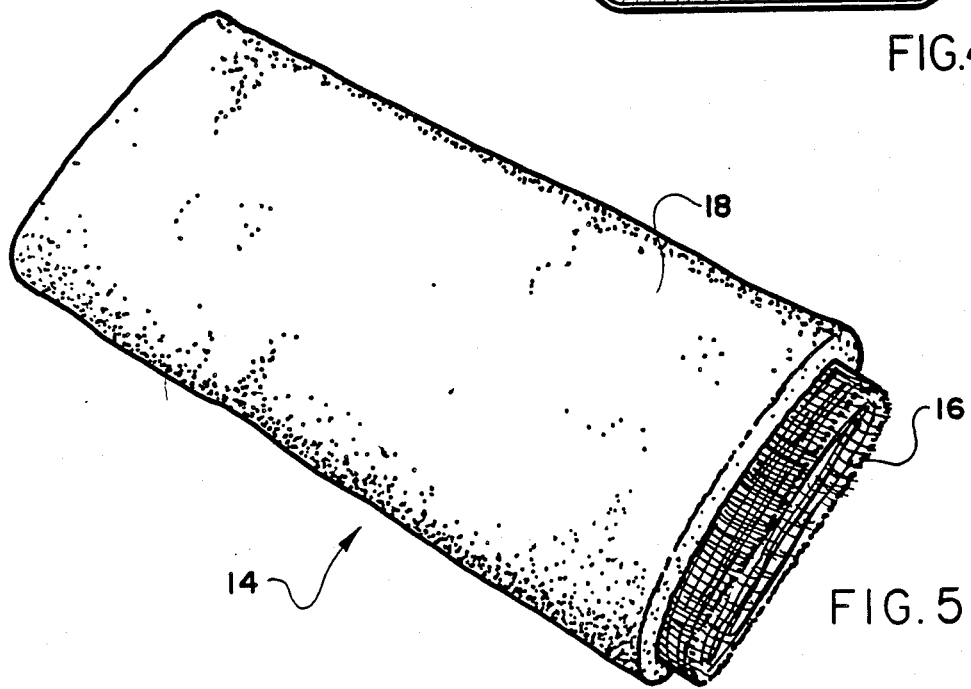
FIG. 5 is a perspective view of a length of the medical material with the substrate layer exposed for clarity.
Figure 6:
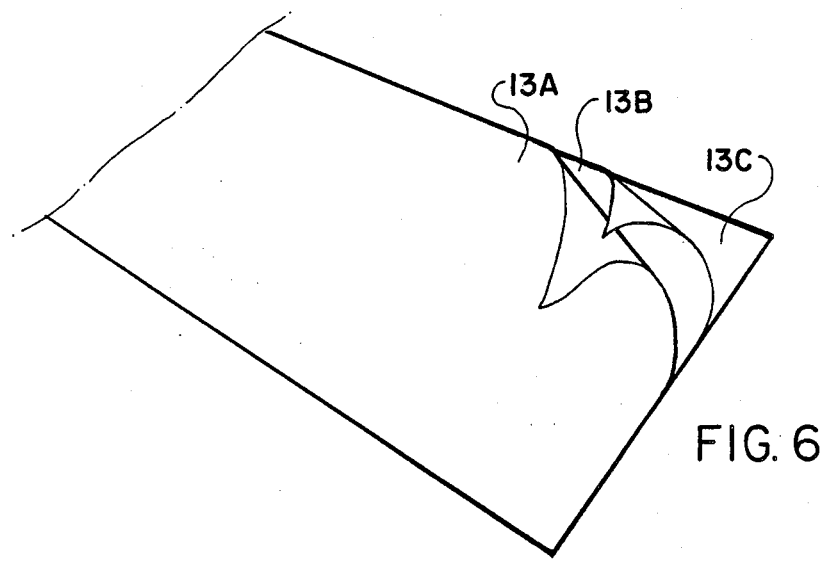
FIG. 6 is a perspective view illustrating the laminate structure of the elongate outer sleeve.

Referring now to FIGS. 4 and 5, medical material 14 comprises a substrate 16 comprised of a suitable number for example, 6, of overlaid layers of a woven or knitted relatively open fabric, such as fiberglass. Substrate 16 is contained within a tubular wrapping 18 which is formed of a soft, flexible non-woven fiber such as polypropylene or some other suitable hydrophobic fiber. This provides a cushioning protective layer between the skin of the patient and substrate 16. Substrate 16 is impregnated or coated with a reactive system which remains stable when maintained in substantially moisture-free conditions but which hardens upon exposure to sufficient moisture to form a rigid, self-supporting structure. A typical formulation of the reaction system is set forth in the following table:

| Typical Formulation: | | |
|---|---|---|
| Isonate ® 143L or | | |
| Mondur ® CD or | polyisocyanate | 50.0% |
| Rubinate ® XI168 | | |
| Pluracol ® P1010 | polyol | 46.6% |
| DC-200 Silicone | defoaming agent | 0.30% |
| Benzoyl Chloride | stabilizer | 0.10% |
| Thancat ® DM-70 | catalyst | 3.0% |
| | | 100% |

A complete discussion of the parameters of the reactive system, the manner of production and the variables which apply are found in U.S. Pat. No. 4,411,262, referred to above.

As in shown in FIG. 3, sleeve 13 is formed of two laminated elongate sheets placed in registration and heat sealed along its opposite sides to form a tube. The outer layer 13a is formed of a tear-resistant plastic film. The middle layer 13b comprises aluminum foil and acts as a moisture barrier. The inner layer 13c is a plastic film having thermoplastic properties suitable for heat sealing the interior of sleeve 13 securely against moisture.

Figure 7:
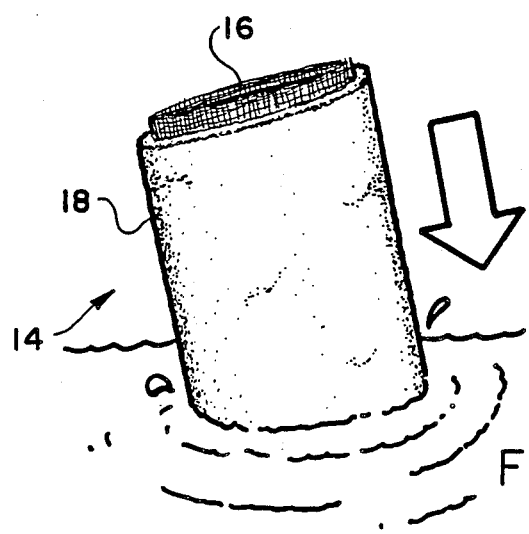
FIG. 7 illustrates activation of the moisture-curable resin of the invention by wetting.

As is shown in FIG. 7, moisture-curing is activated by dipping product 14 in water. Then excess moisture is squeezed from the structure.

Figure 8:
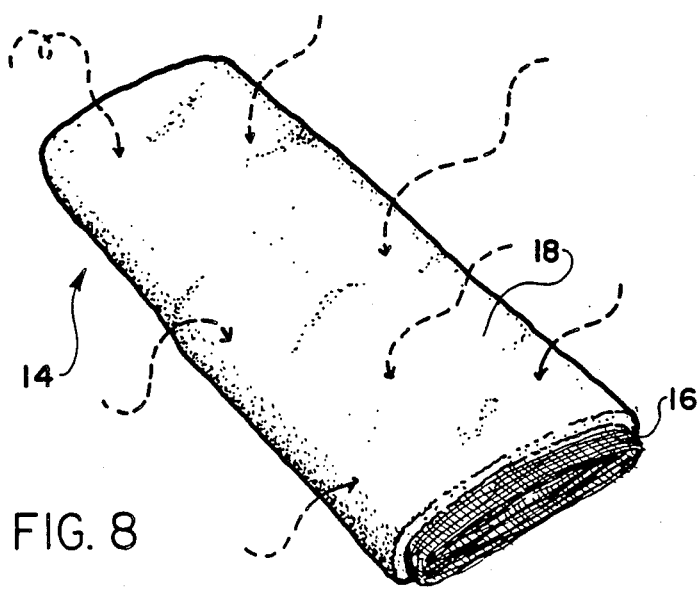
FIG. 8 illustrates activation of the reactive hardening system of the invention by contact with atmospheric moisture.

Alternatively, moisture-curing can take place over a longer period of time by allowing contact between the reactive system on substrate 16 and atmospheric moisture, as is illustrated in FIG. 8.

Figure 9:
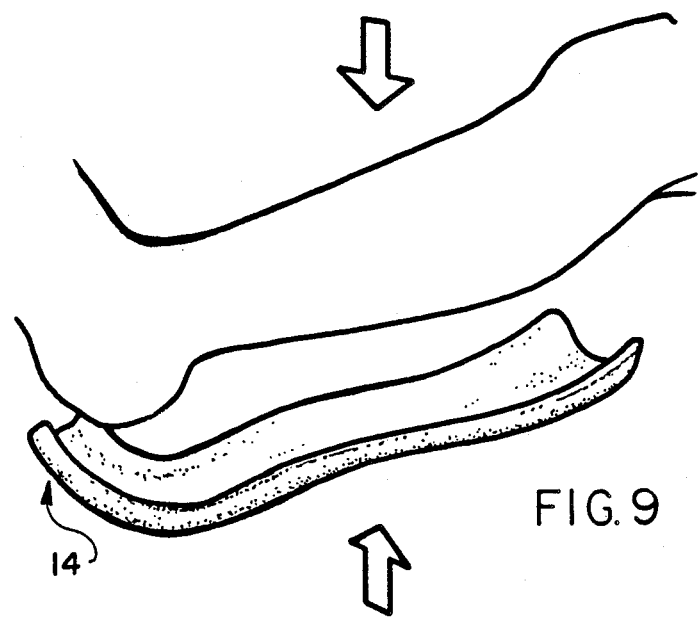
FIG. 9 shows the medical material after removal from the sleeve being formed to fit the contour of a body member.
Figure 10:
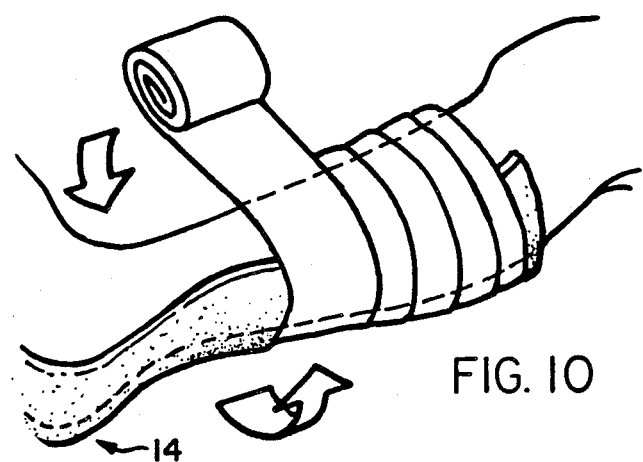
FIG. 10 is a perspective view of the hardening medical material being secured into place on a body member by means of a covering wrap.

Referring now to FIG. 9, an appropriate length of material 14 is formed to the shape of the body member to be immobilized. This particular type of splint, known as a posterior short leg splint, is formed by molding a length of the product 14 to the calf and up over the heel and onto the foot. Then, product 14 is overwrapped with an elastic conventional bandage, as is shown in FIG. 10.

I claim:

1. An elongate medical bandaging product for being dispensed in lengths suitable for a given medical use, comprising:
    (a) an elongate sleeve of a predetermined length formed of moisture-impervious material and sealable to prevent entry of moisture;
    (b) an elongate medical material having substantially the same predetermined length as said elongate sleeve and positioned in a continuous layer which coextends with the sleeve in substantially moisture-free conditions and sealed therein against entry of moisture until use, said medical material comprising:
        (i) a substrate;
        (ii) a reactive system impregnated into or coated onto said substrate, said system remaining stable when maintained in substantially moisture-free conditions and hardening upon exposure to sufficient moisture to form a rigid, self supporting structure; and
        (iii) a soft, flexible protective wrapping enclosing said substrate along its length to provide a cushioning barrier between the substrate and the skin of a patient when the material is in use;
    whereby a desired length of said medical material is removable from a length of the bandaging product by severing the medical material and the sleeve at a desired point without removing additional excess medical material from the sleeve whereby the sleeve and medical material form a continuum of elongate medical bandaging product and whereby said sleeve is sealable against entry of moisture after a desired length of said medical material has been dispensed for use to prevent hardening of said substrate remaining in said sleeve.

2. A medical bandaging product according to claim 1, wherein said sleeve comprises a aluminum foil laminate having an outer tear resistant layer, a central aluminum foil layer and an inner heat sealable plastic layer.

3. A medical bandaging product according to claim 1, wherein said substrate comprises a plurality of knitted or woven fabric layers.

4. A medical bandaging product according to claim 1, wherein said protective wrapping enclosing the substrate comprises a fibrous nonwoven cushion.

5. A medical bandaging product according to claim 4, wherein said protective wrapping enclosing the substrate comprises a nonwoven polypropylene tube.

6. A medical bandaging product according to claim 1, wherein said reactive system comprises a blended polyisocyanate, polyol, catalyst and stabilizer.

7. A medical bandaging product according to claim 1, wherein said means for sealing said sleeve comprises moisture-impervious tape.

8. A medical bandaging product according to claim 1, wherein said medical bandaging product is in the form of a coil.

9. A medical bandaging product according to claim 8, and further including a dispenser within which the coil of bandaging product is contained.

10. A medical bandaging product according to claim 9, wherein said dispenser comprises a container within which said coil is positioned and includes a slot in which a leading end of the coil may be positioned and through which the medical bandaging product is dispensed as needed.

11. An elongate medical bandaging product for being dispensed in lengths suitable for a given medical use, comprising:
    (a) an elongate sleeve of a predetermined length formed of a moisture-impervious aluminum foil laminate having an outer tear resistant plastic layer, a central aluminum foil layer and an inner heat sealable plastic layer and sealable to prevent entry of moisture;
    (b) an elongate medical material having substantially the same predetermined length as said elongate sleeve and positioned in said sleeve in substantially moisture-free conditions and sealed therein against entry of moisture until use, said medical material comprising:
        (i) a substrate formed of a plurality of knitted or woven fabric layers;
        (ii) a reactive system impregnated into or coated onto said substrate, said system remaining stable when maintained in substantially moisture-free conditions and hardening upon exposure to sufficient moisture to form a rigid, self supporting structure and comprising a blended polyisocyanate, polyol, catalyst and stabilizer; and
        (iii) a soft, flexible protective nonwoven tubular web enclosing each substrate along its length to provide a cushioning barrier between the substrate and the skin of a patient when the material is in use;
    whereby a desired length of said medical material is removable from a length of the bandaging product by severing the medical material and the sleeve at a desired point without removing additional excess medical material from the sleeve whereby the sleeve and medical material form a continuum of elongate medical bandaging product and whereby said sleeve is sealable against entry of moisture after a desired length of said medical material has been dispensed for use to prevent hardening of said substrate remaining in said sleeve.

* * * * *